US012708751B2

(12) United States Patent
Daviot

(10) Patent No.: US 12,708,751 B2
(45) Date of Patent: Aug. 18, 2026

(54) MICRONEEDLE APPLICATOR

(71) Applicant: APTAR FRANCE SAS, Le Neubourg (FR)

(72) Inventor: Stéphane Daviot, Graveron Semerville (FR)

(73) Assignee: APTAR FRANCE SAS, Le Neubourg (FR)

( * ) Notice: Subject to any disclaimer, the term of this patent is extended or adjusted under 35 U.S.C. 154(b) by 887 days.

(21) Appl. No.: 18/007,654

(22) PCT Filed: Jun. 1, 2021

(86) PCT No.: PCT/FR2021/050988
§ 371 (c)(1),
(2) Date: Dec. 1, 2022

(87) PCT Pub. No.: WO2021/245346
PCT Pub. Date: Dec. 9, 2021

(65) Prior Publication Data
US 2023/0293870 A1 Sep. 21, 2023

(30) Foreign Application Priority Data
Jun. 2, 2020 (FR) ...................................... 2005784

(51) Int. Cl.
*A61M 37/00* (2006.01)

(52) U.S. Cl.
CPC ............................... *A61M 37/0015* (2013.01)

(58) Field of Classification Search
CPC ................................................ A61M 37/0015
USPC ......................................................... 604/173
See application file for complete search history.

(56) References Cited

U.S. PATENT DOCUMENTS

| | | | | |
|---|---|---|---|---|
| 6,256,533 | B1 * | 7/2001 | Yuzhakov ......... | A61M 37/0015 604/20 |
| 6,558,361 | B1 * | 5/2003 | Yeshurun .......... | A61M 37/0015 604/274 |
| 2011/0295149 | A1 | 12/2011 | Mitragotri et al. | |

(Continued)

FOREIGN PATENT DOCUMENTS

| | | | |
|---|---|---|---|
| KR | 10-2018-0136722 | A | 12/2018 |
| WO | 2016/049732 | A1 | 4/2016 |

OTHER PUBLICATIONS

International Search Report for PCT/FR2021/050988 dated Sep. 28, 2021.

(Continued)

*Primary Examiner* — Phillip A Gray
(74) *Attorney, Agent, or Firm* — Sughrue Mion, PLLC

(57) ABSTRACT

A microneedle applicator for applying a fluid product to the skin and causing the fluid product to penetrate to the skin. The applicator has an application face provided with at least one fluid product outlet; a plurality of microneedles; a fluid product reservoir connected to the fluid product outlet; and a motor for causing the microneedles to vibrate and to convey the fluid product from the reservoir to the outlet. The applicator has two distinct modules axially and removably connected to each other, namely, a first module housing the motor and accessories for operating the motor; and a second module housing the fluid product reservoir, forming the application face and supporting the microneedles.

16 Claims, 5 Drawing Sheets

(56) References Cited

U.S. PATENT DOCUMENTS

2012/0046644 A1 2/2012 Ziaie et al.
2019/0201615 A1* 7/2019 You .................. A61M 37/0015

OTHER PUBLICATIONS

International Preliminary Report on Patentability dated Sep. 16, 2022 in Application No. PCT/FR2021/050988.

* cited by examiner

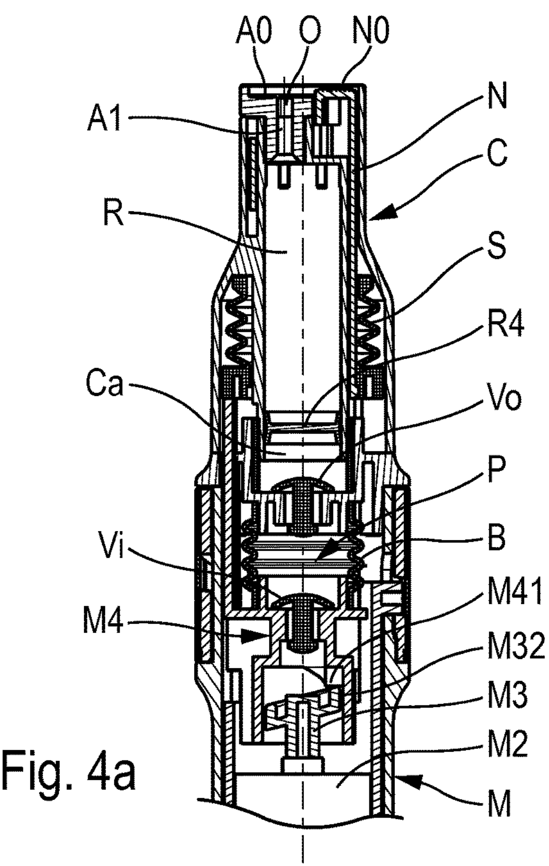
A0
O
N0
N
A1
C
R
S
R4
Ca
Vo
P
B
Vi
M41
M4
M32
M3
M2
M
Fig. 4a
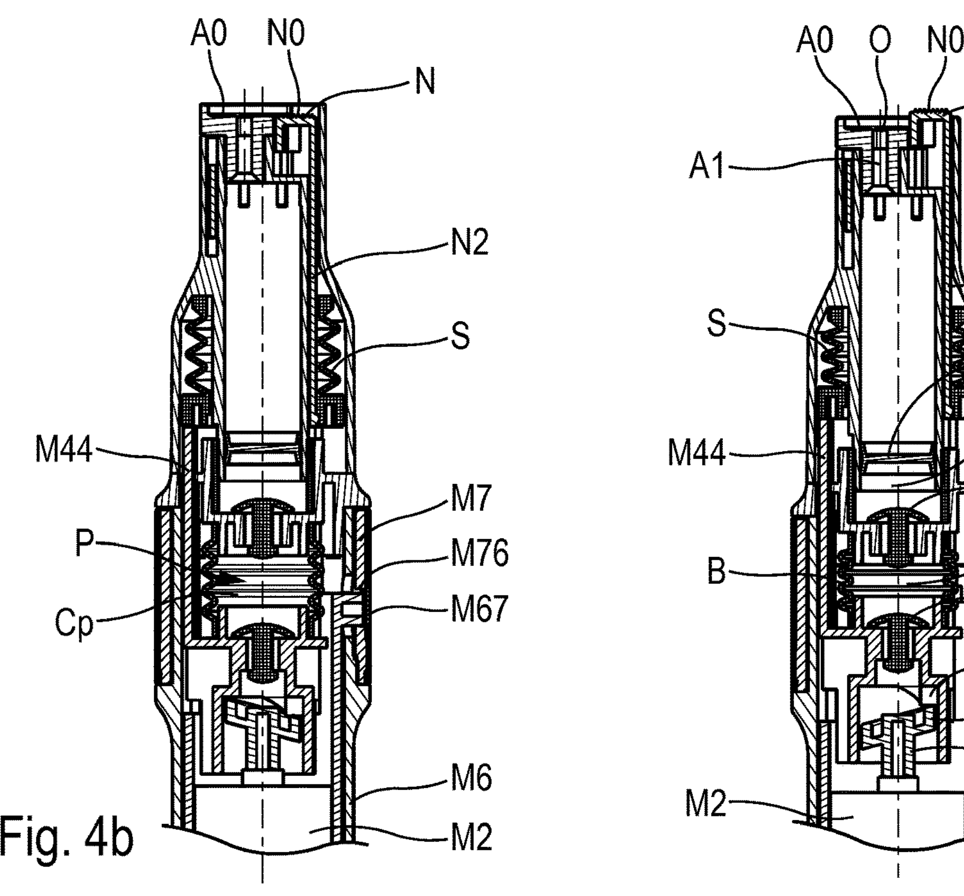
A0
N0
N
N2
S
M44
M7
P
M76
Cp
M67
M6
M2
Fig. 4b
A0
O
N0
N
A1
N2
S
R4
Ca
M44
Vo
Cp
B
Vi
M41
M31
M3
M2
Fig. 4c

MICRONEEDLE APPLICATOR

CROSS REFERENCE TO RELATED APPLICATIONS

This application is a National Stage of International Application No. PCT/FR2021/050988 filed Jun. 1, 2021, claiming priority based on French Patent Application No. 2005784 filed Jun. 2, 2020.

The present invention relates to a microneedle applicator for applying a fluid product on the skin and for making it penetrate into the epidermis. The field of application of the invention is that of cosmetics, and not that of tattooing. The aim is to allow a cosmetic treatment to penetrate into the skin, and not to colour the skin.

Conventionally, this type of cosmetic applicator comprises an application face provided with at least one fluid product outlet and a plurality of microneedles. An electric motor is used to make the microneedles vibrate, individually or with the application face. A fluid product reservoir is connected to the fluid product outlet. The reservoir may be integrated or not to the applicator. When it is integrated, the question is thus asked about it being filled or it being replaced. The applicator may be dismountable or comprise a window or a stopper for accessing the reservoir.

On the other hand, an actuating member is also provided to convey the fluid product from the fluid product reservoir to the fluid product outlet. This actuating member is often the component which also controls the motor, which thus accumulates a dual function, namely, to make the microneedles vibrate and to convey the fluid product from the reservoir to the application face.

The present invention aims to propose an applicator with a dual-function motor, the reservoir of which is easily replaceable, while providing a simple, effective and robust connection between the motor and the reservoir. The use of the applicator, and in particular the replacement of the reservoir, must not lead to any accidental deterioration of this motor/reservoir connection.

To achieve this aim, the present invention proposes a microneedle applicator for applying a fluid product on the skin and for making it penetrate into the skin, the applicator defining a longitudinal axis and comprising:

- an application face provided with at least one fluid product outlet;
- a plurality of microneedles;
- a fluid product reservoir is connected to the fluid product outlet;
- a motor for causing the microneedles to vibrate and to convey the fluid product from the reservoir to the outlet, characterised in that it comprises two distinct modules axially connected to one another, namely:

- a motor module housing the motor and the accessories to make the motor function; and
- a second module housing the fluid product reservoir, forming the application face and supporting the microneedles.

Thus, the second module may be considered as a cartridge or a refill which is replaced, while the first module with its motor is kept.

Advantageously, the fluid reservoir has a variable volume, the actuation of the motor acting on the reservoir without any mechanical transmission of a force, to lead to a decrease in volume of the fluid product reservoir, such that some of its content is repelled to the fluid product outlet. In other words, there is no part or member which connects the motor to the reservoir to transmit the force generated by the motor. Thus, there is no risk of damaging the transmission, since it is not material.

Advantageously, the first module may comprise an air pump. On the other hand, the fluid product reservoir may comprise a movable wall which also forms part of an air chamber supplied with pressurised air coming from the air pump. Preferably, the air chamber is formed jointly by the two modules connected in sealed manner. The transmission may thus be hydraulic, as opposed to being mechanical. The pressurised air in the air chamber will push and move the movable wall of the reservoir, which may be in the form of a pusher piston or a flexible pouch, for example. The art is to form this air chamber between the two modules, such that there is no mechanical transmission part or member which is accessible and therefore easily damaged, when the two modules are separated from each other. To constitute the air chamber, it suffices to create a seal between the two modules.

According to a practical embodiment, the air pump may comprise a pump chamber (Cp) equipped with an air inlet valve and an air outlet valve connected to the air chamber, the variation in volume of the pump chamber being advantageously provided by a bellows. A piston which slides in a cylinder may replace the bellows. Advantageously, the air inlet valve may be driven axially back and forth by the motor. In a practical implementation, the motor may comprise an axial shaft driven in rotation, a system for transforming rotary movement into axial movement being mounted on the rotary shaft. Advantageously, the air pump may comprise a piston which may be moved axially back and forth under the action of the motor, this piston forming a seat for the air inlet valve, a support for a bellows, and transmission means for driving the microneedles of the second module in vibration.

Thus, a purely rotary movement is converted into a reciprocating vibratory movement to actuate an air pump which sends pressurised air into an air chamber common to the two modules, the movable wall also of which forms part of a reservoir of variable volume.

According to another characteristic of the invention, the first module may comprise means for neutralising the air pump to prevent it from supplying the air chamber with pressurised air, advantageously by blocking its air inlet valve in the open position.

According to another aspect of the invention, the first module may further comprise means for adjusting the penetration depth of the microneedles, acting advantageously on the axial position of the motor in the first module.

According to another aspect of the invention, the first module may comprise engagement/disengagement means for engaging/disengaging the transmission of the vibrations generated by the motor to the microneedles.

Advantageously, the air pump may be neutralised when the microneedles are engaged with the motor. In a symmetrical manner, the air pump may supply the air chamber with pressurised air when the microneedles are disengaged from the motor.

According to another characteristic, the application face is attached and the microneedles are mounted on a needle holder driven back and forth by the motor.

Advantageously, the microneedles are mounted on a needle holder which extends around the fluid product reservoir.

The spirit of the invention resides in designing the applicator in the form of two separable modules. This makes it possible to create an air chamber within them, which will serve as a force transmission means, without any mechanical or physical member, since it is the pressurised air which will act on the reservoir.

The invention will now be fully described in reference to the appended drawings which give, as non-limiting examples, a plurality of embodiments of the invention.

Figures 1, 2:
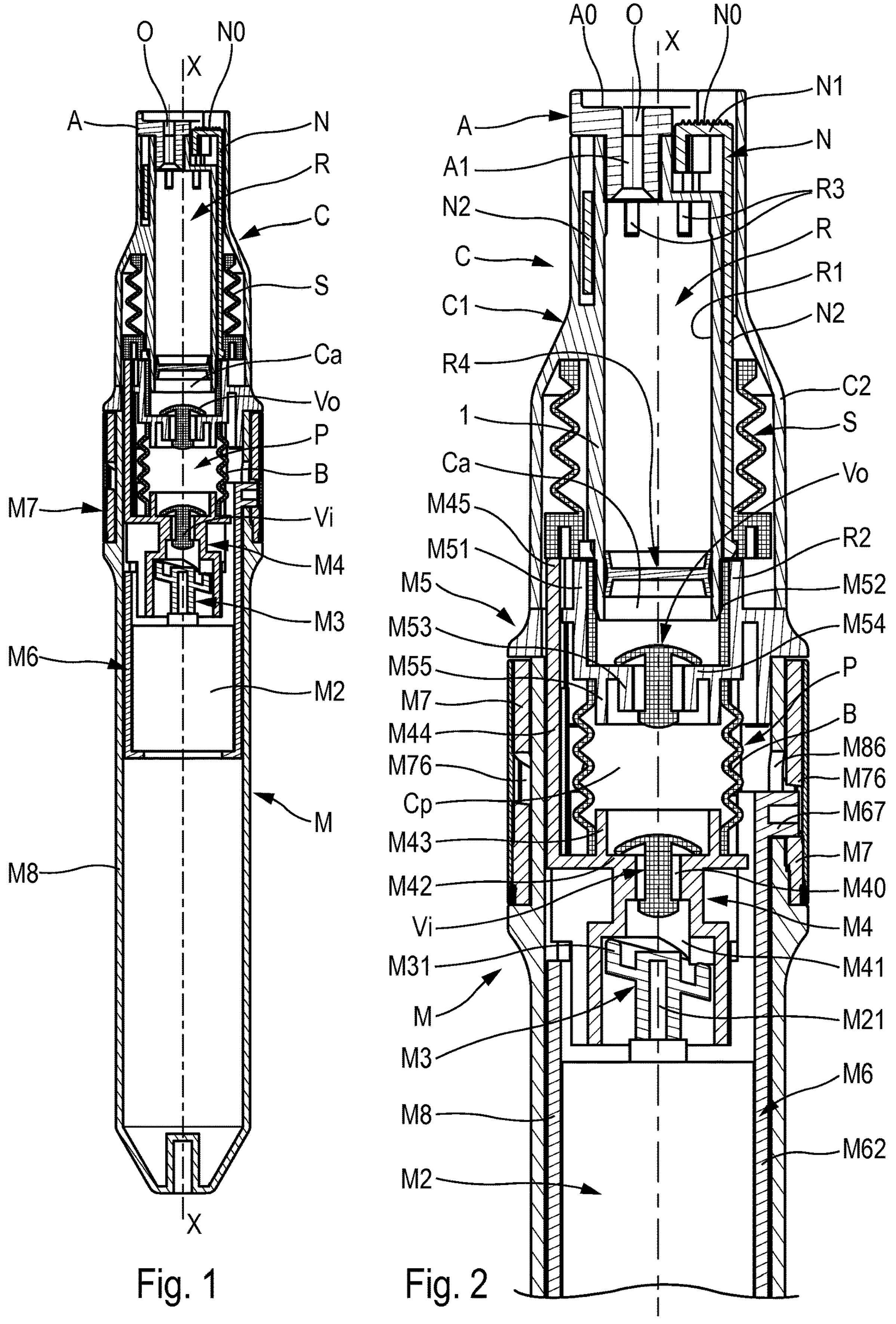
FIG. 1 is a vertical cross-sectional view through an applicator of the invention, in the assembled, and rest state.
FIG. 2 is a large-scale truncated view of the applicator in FIG. 1.
Figure 3:
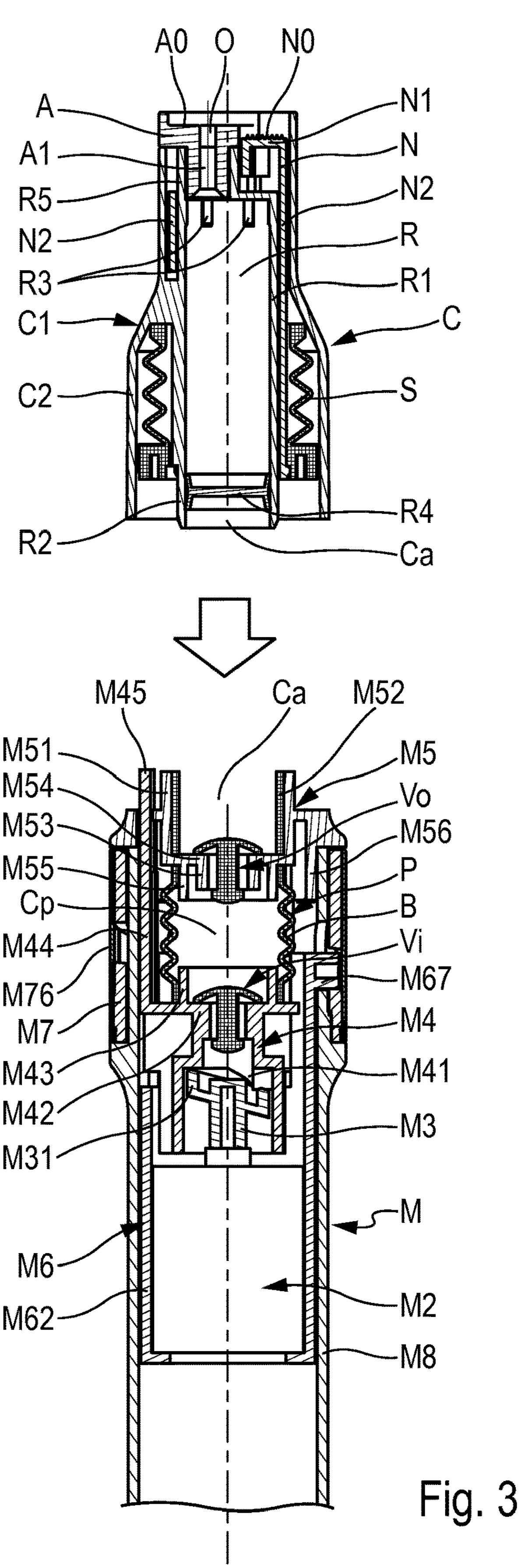
FIG. 3 is a view similar to FIGS. 1 and 2, in the separated state.
Figure 5:
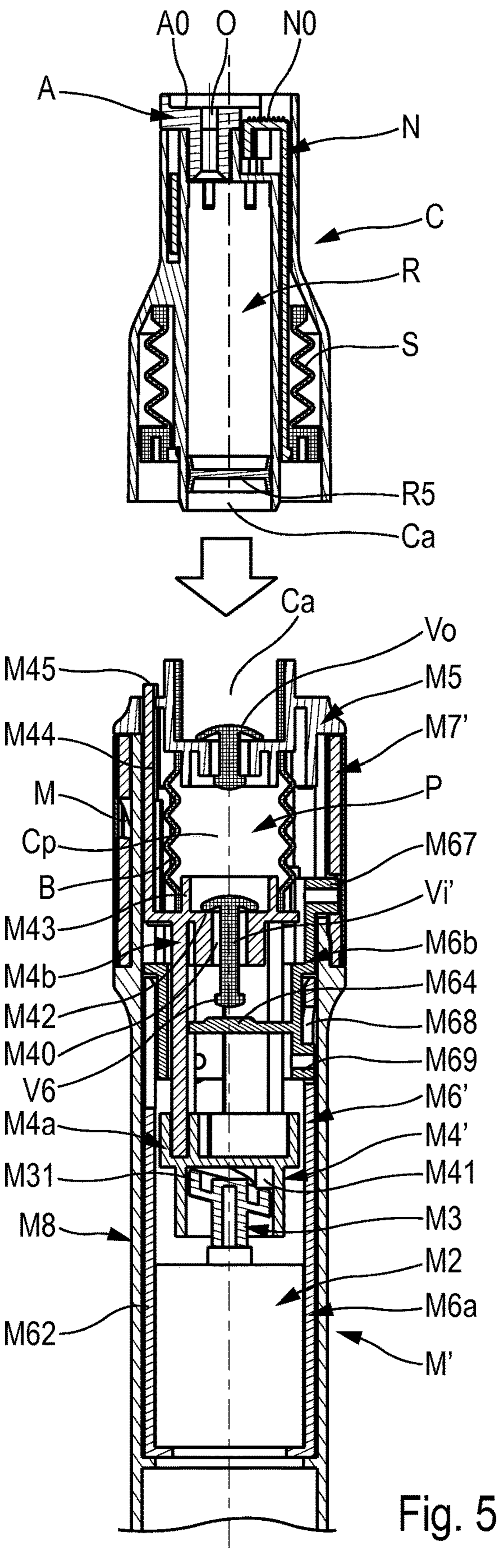
Figure 6C:
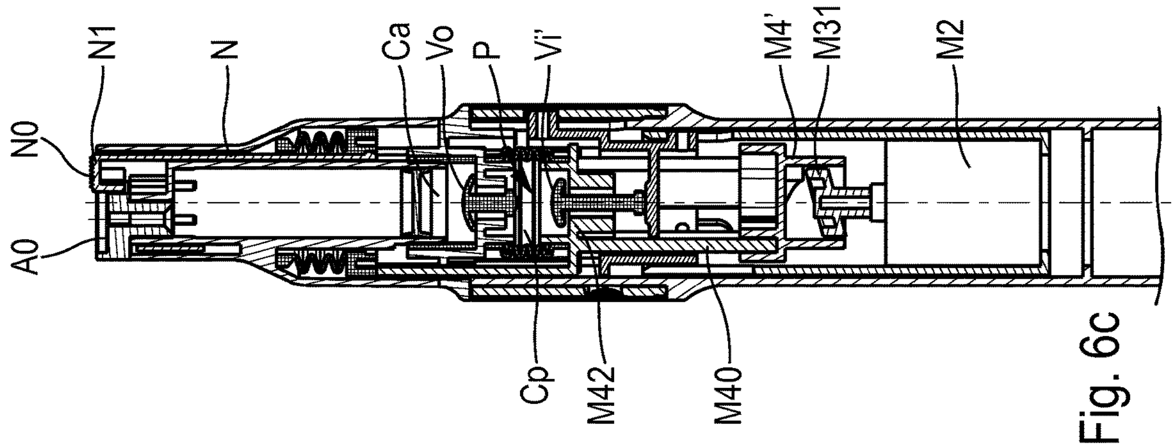
Figure 6B:
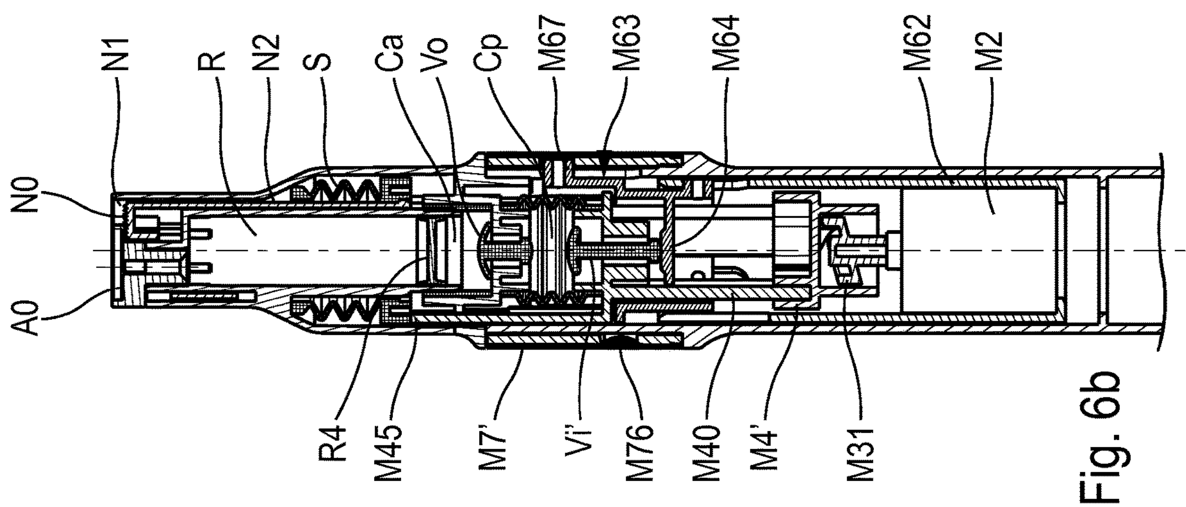
Figure 6A:
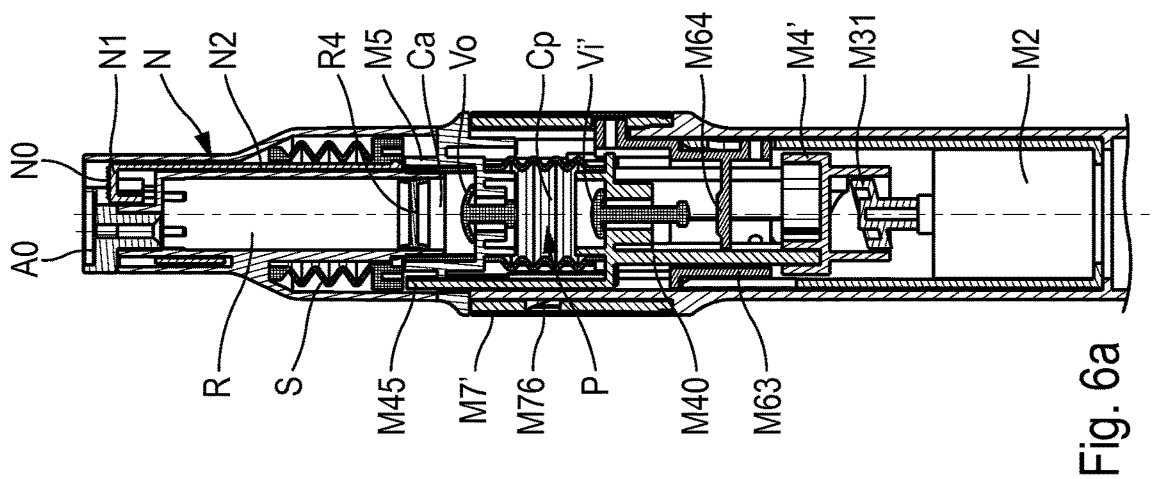

FIGS. 4*a*, 4*b* and 4*c* are views similar to that of FIG. 1 showing the applicator in a different states;

FIG. 5 is a view similar to the view in FIG. 3 for an applicator according a variant embodiment of the invention, and FIGS. 6*a*, 6*b*, and 6*c* are views similar to the views in FIGS. 4*a*, 4*b*, and 4*c* the applicator of FIG. 5.

The applicator of the invention is purely cosmetic, even dermatological, excluding tattooing. It associates two treatment means, namely the distribution of a cosmetic product, which may be a cream, a balm, a lotion, a serum, etc., and the perforation of the epidermis possibly the dermis, without touching the hypodermis, by means of microneedles. The cosmetic product is applied either before, at the same time and/or optionally after the perforation. The applicator of the invention is rather for domestic use, in that the user of the applicator will use it on itself. It can, however, be used professionally.

Reference is made firstly to FIGS. 1 and 2 to describe in detail the first embodiment of the invention. The applicator of the invention comprises two distinct modules, namely a first module M and a second module C, which may be connected and disconnected simply and rapidly, by the user themselves, for example using both their hands by impressing a torque and/or a thrust/traction between two modules. When the two modules are assembled, the applicator has a general, pen-shaped configuration with a longitudinal axis X. The applicator may moreover be held in the same way as a pen, held between the thumb and the middle finger with the index finger resting on the applicator.

The first module M comprises an outer shell M8 that is substantially cylindrical. At its upper end, the shell M8 is open, and closed at its lower end. The shell M8 comprises a side window M86, which may be extended vertically to receive a stud M67, as described below. The outer shell 8, at its side window M86, is surrounded by a selector M7, which is in the form of a rotary ring, which may be rotated by the user, as described below.

The first module M contains a motor M2, preferably an electric motor. It may be a small rotary motor which rotates a shaft M21 on itself. An electromagnet motor may also be provided, a linear or a piezoelectric motor. The motor M2 is powered by a battery (not shown) and controlled by electronics (not shown), which will manage the rotation speed of the shaft (not shown), the activation sequences and durations of the motor, etc. An outer activation button M21 allows the user to switch the applicator on. The free end of the shaft M21 is covered by an oscillating cap M3, which forms a sloped head M31. The rotation of the shaft M21 drives this sloped head M31 in rotation around its own axis, thus describing a rotary oscillating movement.

Advantageously, the motor M2 and the oscillating cap M3 are mounted on a movable carriage M6, which is movable along the longitudinal axis X. The movable carriage M6 comprises a basket M62 which receives the motor M2 and a stud M67 which passes through the side window M86 of the outer shell M8 and penetrates into a cam path M76 formed by the selector M7. The cam path M76 is sloped, such which the rotation of the selector M7 around the shell M8 has the effect of axially moving the stud M67, because it is enclosed in the extended side window M86. As a result, the carriage M6, with its motor M2 and its cap M3, is moved axially inside the outer shell M8. The function of this axial movement is described below. However, the movable carriage M6 is optional.

The first module M also comprises a transmission piston M4 which moves axially back and forth. The piston M4 forms a sloped lower surface M41 which is engaged with the sloped head M31 of the oscillating cap M3. The piston M4 is prevented from rotating, so that the sloped surface M41 remains stationary in rotation, while the sloped head M31 is driven in rotation by the motor M2. As a result, the piston M4 is driven in axial movement, due to the oscillating contact between the sloped head M31 and the sloped surface M41. The piston M4 forms an inlet duct M40 and a seat M42 for an air inlet valve Vi. This valve M42 is surrounded by a bellows support M43. The piston M4 also comprises transmission means M44, which may be in the form of a plurality of (between 2 and 6) axial tabs or rods defining free contact ends M45. The transmission means M44 may slide in contact with the inner wall of the outer shell M8.

The first module M also comprises a ferrule M5 which defines a portion of an air chamber Ca. The ferrule M5 comprises a cylinder M51 which may be internally lined by a sealing sheath M52. The ferrule M5 forms an outlet duct M53 and a seat M54 for an air inlet valve Vo. The ferrule also comprises a bellows support M55. The ferrule M5 is securely held in the outer shell M8 by a cuff M56. The ferrule M5 may be used to prevent the transmission piston M4 from rotating. The contact ends M55 of the transmission means M44 of the piston M4 may, for example, pass through windows of the ferrule M5 around the cylinder M51.

In the invention, the first module M incorporates an air pump P which is defined between the transmission piston M4 and the ferrule M5. More precisely, the air pump P comprises a bellows B which is mounted in sealed manner on the two bellows supports M43 and M55. A pump chamber Cp is therefore defined. It is fed upstream by air passing through the air inlet duct M40 and is controlled by the air inlet valve Vi. The air compressed during the squeezing of the bellows B is forced through the air outlet duct M53 which is controlled by the outlet valve Vo. The squeezing of the bellows B results from the axial movement of the piston M4 with respect to the shell M5, which remains stationary. The bellows B is thus successively squeezed and stretched by the reciprocating movement of the piston M4, which is subjected to the oscillating rotation of the cap M3 driven by the shaft M21 of the motor M2. It may then easily be understood that pressurised air is dispensed by the air pump P into the air chamber Ca.

The actuation of the selector M7 has the effect of forcing the motor M2, its cap M3 and the piston M4 to move axially, thus varying the volume of the pump chamber Cp and extending or retracting the contact ends M45.

The second module or cartridge C contains no electrical or electronic members (s) or component (s): it may be said that it is passive and thus inexpensive. This second module C incorporates a fluid reservoir R which contains a fluid product, preferably cosmetic, which advantageously has a high viscosity: it may be a gel, a cream, an ointment, an oil, etc. The reservoir has a variable volume: this means that its useful volume decreases as the fluid product is extracted from it. The fluid product therefore remains out of contact with the air. The reservoir comprises a movable wall on which a force may be exerted to pressurise the fluid product which is contained in the reservoir and repel a portion outwards. The movable wall is therefore used as a means for pressurising the reservoir, unlike a movable wall which moves in response to a vacuum generated in the reservoir. According to the invention, the movable wall of the reservoir also forms part of the air chamber Ca, defined above.

In the embodiment used to illustrate the present invention, the movable wall is a pusher piston R4 which slides in sealed manner in a slide cylinder R1, which defines at its lower end a sealing bushing R2, intended to engage in sealed manner with the sealing sheath M52 of the ferrule M5, in such a manner as to constitute the air chamber Ca. Advantageously, the cylinder R1 comprises a plurality of vent ribs R3 at its upper end to create a leakage path when the pusher piston R4 reaches the level thereof. This avoids creating excessive overpressure within the air chamber Ca. It can be seen from the figures that the cylinder R1 is formed by a body C1, which also forms an outer fairing C2, which surrounds the cylinder R1, defining the reception spaces between them. A return spring S is housed in the lower space; its upper end is securely connected to the body C1, while its lower end is free and may therefore move axially by compressing the spring. The lower end of the spring S is connected to transmission means N2, which may be in the form of a plurality of (between 2 and 6) axial tabs or rods which may slide between the cylinder R1 and the fairing C2. These transmission means N2 form an integral part of the needle holder N, which also forms a support face N1 provided with a plurality of microneedles NO. Their number may vary from 5 to 100. Their thickness may vary from 0.05 mm to 0.5 mm. Their length may vary from 0.1 mm to 0.7 mm. These values are given for information purposes only. The support face N1 is located axially above the reservoir R, on the right-hand side of the figures. It is understood that the microneedles NO may move axially upwards against the elastic force exerted by the return spring S. In the rest position, the support face N1 abuts against the top of the reservoir.

It should be noted that the reservoir R occupies a central or axial position, while the transmission means N2 extend around and along the reservoir R.

The second module or cartridge C also comprises an application endpiece A, which is securely mounted at the top of the cylinder R1, which forms a mounting funnel R5 for this purpose. The application endpiece A forms an outlet channel A1 which defines an outlet for the fluid product O which opens out at an application face A0. Thus, the fluid product stored in the reservoir R is pressurised by the movement of the pusher piston R4 which is subjected to the overpressure that exists in the air chamber Ca. In response, a portion of the fluid is forced through the outlet channel A1 and the outlet O to reach the application face A0.

It can be seen in FIG. 3 that the two modules M and C are two distinct entities, which may be connected axially with a relative movement indicated by the arrow visible between them. During this movement, the sealing bushing R2 penetrates into the sheath M52, creating a sealing contact between them: the air chamber Ca is thus formed. At the same time, the lower edge of the fairing C2 comes into abutment contact or snap-fastening contact with the ferrule M5: a stable connection is thus established. The applicator is then in the mounted rest state shown in FIGS. 1 and 2, with the selector M7 in the low position. The oscillating cap M3 is in an angular position which corresponds to the bottom dead centre of the stroke of the transmission piston M4. The support face N1, with its microneedles NO, is then in the maximum low position. It may be observed in FIGS. 1 and 2 that the support face N1 is offset axially downwards with respect to the application face AO. The pump chamber Cp is in a maximum-volume state. On the other hand, it can be seen that the contact ends M45 of the transmission means M44 of the piston M4 are in contact with the lower end of the return spring S, which is connected to the transmission means N2 of the needle holder N.

In FIG. 4*a*, the applicator in FIGS. 1 and 2 has been actuated: its motor M2 has made half a turn, which has the effect of causing the oscillating cap M3 to rotate, thereby pushing the transmission piston M4 into the maximum high position. The axial movement of the piston M4 has two distinct but simultaneous effects. The first effect is to transmit the force exerted by the motor M2 through the oscillating cap M3, which transforms a rotation into axial movement, directly to the needle holder N, such that the microneedles NO begin to vibrate axially. The second effect is to actuate the air pump P, which will send pressurised air into the air chamber Ca, which will push the pusher piston R4 into the cylinder R1 to deliver fluid product onto the application face A0. FIG. 4*a* shows the applicator when the support face N1 is in the most extended position and the pump chamber in the minimum-volume state.

In FIG. 4*b*, the selector M7 has been actuated: the stud M67 of the carriage M6 has been driven upwards under the stress of the cam path M76. The motor M2, its cap M3 and the transmission piston M4 have been moved axially upwards. The bellows B has been slightly squeezed, such that the maximum effective volume of the pump chamber Cp has decreased slightly. Furthermore, the transmission piston M4 has moved the needle holder N, such that the support face N1 is higher than in FIGS. 1 and 2: it is substantially or exactly at the same level as the application face AO, whereas the transmission piston M4 is in the low position.

In FIG. 4*c*, the applicator in FIG. 4*b* has been actuated by half a turn. The pump chamber Cp is in the minimum-volume state and the support face N1 is in its maximum extended position. It can be seen that it is higher than in FIG. 4*a*. The fluid is dispensed to the application face by pressurising the air chamber Ca and moving the pusher piston R4, whereas the microneedles NO will penetrate deeper into the skin because of their advanced or extended position.

The selector M7 therefore acts on the penetration depth of the microneedles NO. The user may personally adjust this depth depending on various parameters, such as the nature of the skin, its suppleness, the nature of the fluid product, the desired result, etc.

It should especially be noted that the transmission of force between the two modules is ensured without mechanical connection, such as a rod or a tube which would project out of the first module to be able to penetrate into the second module and push the movable wall of the reservoir. Such a mechanical connection may be damaged when the two modules are separated. Furthermore, this mechanical connection should be pushed back or returned to its initial position each time the cartridge is replaced. With the invention, which provides a non-mechanical transmission, all these disadvantages are eliminated. Pressurised air is a means of transmitting force which cannot be damaged and does not need to be returned to the initial position.

Reference is made below to FIG. 5 in order to describe a variant embodiment of an applicator according to the invention. The applicator is always made in the form of two distinct separable modules. The second module or cartridge C may be is similar or identical to that of the first embodiment. And is therefore not described. As for the first module M', the motor M2, the oscillating cap M3, the ferrule M5, the air outlet valve Vo and the outer shell M8 may be similar or identical to those of the first embodiment. Even the selector M7' may be identical, but have a different function. The transmission piston M4 of the first embodiment has been replaced by a two-piece transmission piston M4', namely a lower portion M4*a* and an upper portion M4*b*. Similarly, the carriage M6 of the first embodiment has been replaced by a two-piece carriage M6', namely a basket M6*a* and a valve actuator M6*b*.

In greater detail, the lower portion M4*a* of the transmission piston M4' forms the sloped surface M41 which engages with the sloped head of the oscillating cap M3. The upper portion M4*b* is securely mounted on the lower portion M4*a* and forms an inlet duct M40, a seat M42 for an air inlet valve Vi', a bellows support M43 and transmission means M44 defining free contact ends M45, as in the first embodiment.

The basket M6*a* of the carriage M6' forms a housing M62 for the motor M2, its oscillating cap M3, the lower portion M3*a* of the transmission piston M4' and also the lower part of the upper portion M4*b*. The valve actuator M6*b* is mounted with limited sliding in the basket M6*a*. It comprises a stud M67 engaged in the cam path M76 of the selector M7', and a thrust finger M64 which extends below the air inlet valve Vi'. For this purpose, the valve member Vi' comprises a lower stub V6 which is intended to come into contact with the thrust finger M64 to detach the valve Vi' from its seat M42, as described below. The basket M6*a* forms an extended opening M68, and the valve actuator M6*b* comprises a pin M69 engaged in the extended opening M68, so as to be able to move axially over a limited stroke.

FIG. 6*a* is similar to FIG. 4*a*: The selector M7' is in the low position and the motor M2 has rotated by half a turn, so that the piston M4' is in the maximum high position. The pump P has been actuated and pressurised air has been injected into the air chamber Ca to push the pusher piston R4 and deliver fluid product onto the application face AO. However, the needle holder N remains stationary, given that the contact ends M45 are out of contact with the needle holder N, even in the high position of the piston M4'. In fact, it should be noted in FIG. 6*a* that a small gap remains between the end M45 and the return spring S. It should also be noted that the spring is in abutment against the ferrule M5. Thus, the applicator is in a configuration in which it dispenses fluid product only: the air pump operates normally, whereas the microneedles NO remain stationary or inactive. The user may thus use the applicator without micro-perforation.

In FIG. 6*b*, the selector M7' has been actuated: the stud M67 of the carriage M6' has been driven upwards under the stress of the cam path M76. The motor M2, its cap M3 and the transmission piston M4 have been moved axially upwards. The contact end M45 of the transmission piston M4 is now in contact with the lower end of the return spring S. The needle holder N has been moved upwards, so that the support face N1 is now substantially or exactly at the same level as the application face AO, whereas the transmission piston M4' is in the low position with respect to the oscillating cap M3. At the same time, the thrust finger M64 has separated the air inlet valve Vi' from its seat, such that it can no longer perform the selective sealing function during the increased pressure stages within the pump chamber Cp. The movement of the thrust finger M64 with respect to the piston M4' is possible, because the valve actuator M6*b* moves over a small limited axial stroke with respect to the basket M6*a*.

In FIG. 6*c*, the applicator in FIG. 6*b* has been actuated by half a turn. The cap M3 and the piston M4' have been moved upwards, compressing the spring S and moving the needle holder N. It can be seen that the support face N1 is in a higher position than in FIG. 6*b* and that the microneedles NO project out with respect to the application face AO. However, the air pump P has not sent pressurised air into the air chamber Ca. Indeed, its inlet valve Vi' is detached from its seat M42, such that the pump chamber Cp cannot be pressurised. The air entering through the inlet valve Vi' again leaves as soon as the bellows B is squeezed. Thus, the applicator is in a configuration in which it does not dispense the fluid product: only the microneedles NO remain activated. The user may thus use the applicator without dispensing doses of fluid.

The selector M7' acts as a permutation means, making it possible to switch from dispensing a fluid product to microperforation, without it being possible to implement both simultaneously.

In a variant, a permutation between distribution (individual) and distribution/perforation is possible by simply eliminating the thrust finger M64.

Without going beyond the scope of the invention, it is possible to combine the depth adjustment of penetration by means of the permutation. It is very easy to envisage a third position for the selector M7', in which the needle holder N is extended or advanced as in the first embodiment. There would then be three positions with the following configurations:

Rest: individual dispensing or dispensing/perforation;

Intermediate: dispensing/perforation or individual perforation;

Advanced: deep dispensing/perforation or deep perforation only.

In the embodiments described above, the accessories which are used to power and control the motor are not shown. However, it is possible to envisage using the motor control to sequence the distribution and perforation phases: the duration and the course of the sequences may be controlled by a dedicated microprocessor.

NOMENCLATURE OF REFERENCES

Module 1: M; M'

Motor: M2—Motor shaft: M21

Oscillating cap: M3—Sloped head: M31

Transmission piston: M4; M4'—Lower portion M4*a*—Upper portion: M4*b*—Inlet duct: M40—Sloped surface: M41—Valve seat: M42—Bellows support: M43—Means of transmission: M44—Contact end: M45

Air pump: P—Pumping chamber: Cp—Inlet valve: Vi; Vi'—Outlet valve: Vo—Bellows: B Ferrule: M5—Cylinder: M51—Sealing sheath: M52—Outlet duct: M53—Outlet valve seat: M54—Bellows support: M55

Air chamber: Ca

Carriage: M6; M6'—Basket: M6*a*—Valve actuator: M6*b*—Housing: M62—Stud: M67—Thrust finger: M64

Selector: M7; M7'—Cam path: M76
Outer shell: M8—Side window M86
Second module (cartridge): C
Fluid product reservoir: R—Slide cylinder: R1—Sealing bushing: R2—Vent ribs: R3—Pusher piston: R4
Body: C1—Fairing: C2
Application endpiece: A—Outlet channel: A1—Application face: AO—Fluid product outlet: O
Needle holder: N—Microneedles: NO—Support face: N1—Means of transmission: N2
Return spring: S

The invention claimed is:

1. A microneedle applicator for applying a fluid product on the skin and for making it penetrate into the skin, the applicator defining a longitudinal axis X and comprising:

an application face provided with at least one fluid product outlet;

a plurality of microneedles;

a fluid product reservoir connected to the fluid product outlet;

a motor for causing the microneedles to vibrate and to convey the fluid product from the reservoir to the outlet;

and being characterised in that it comprises two distinct modules axially and removably connected to each other, namely:

a first module housing the motor and accessories for operating the motor; and a second module housing the fluid product reservoir, forming the application face and supporting the microneedles.

2. The applicator according to claim 1, wherein the fluid product reservoir has a variable volume, the actuation of the motor acting on the fluid product reservoir without any mechanical transmission, to lead to a decrease in volume of the fluid product reservoir, such that some of its content is repelled to the fluid product outlet.

3. The applicator according to claim 2, wherein the first module comprises an air pump.

4. The applicator according to claim 3, wherein the fluid product reservoir comprises a movable wall that also forms part of an air chamber supplied with pressurised air from the air pump.

5. The applicator according to claim 4, wherein the air chamber is formed jointly by the two modules connected in a sealed manner.

6. The applicator according to claim 5, wherein the air pump comprises a pump chamber equipped with an air inlet valve and an air outlet valve connected to the air chamber, the variation in volume of the pump chamber being advantageously provided by a bellows.

7. The applicator according to claim 6, wherein the air inlet valve is driven axially back and forth by the motor.

8. The applicator according to claim 1, wherein the motor comprises an axial shaft driven in rotation, a rotary to axial motion transformation system being mounted on the rotary shaft.

9. The applicator according to claim 6, wherein the first module comprises means for neutralising the air pump to prevent it from supplying the air chamber with pressurised air, advantageously by blocking its air inlet valve in the open position.

10. The applicator according to claim 1, wherein the first module comprises means for adjusting the penetration depth of the microneedles, acting advantageously on the axial position of the motor in the first module.

11. The applicator according to claim 1, wherein the first module comprises engagement/disengagement means for engaging/disengaging the transmission of the vibrations generated by the motor to the microneedles.

12. The applicator according to claim 9, wherein the air pump is neutralised when the microneedles are engaged with the motor.

13. The applicator according to claim 9, wherein the air pump supplies the air chamber with pressurised air when the microneedles are disengaged from the motor.

14. The applicator according to claim 1, wherein the application face is attached and the microneedles are mounted on a needle holder driven back and forth by the motor.

15. The applicator according to claim 1, wherein the microneedles are mounted on a needle holder which extends around the fluid product reservoir.

16. The applicator according to claim 6, wherein the first module comprises a piston which may be moved axially back and forth under the action of the motor, this piston forming a seat for the air inlet valve, a support for a bellows, and transmission means for driving the microneedles of the second module in vibration.

* * * * *